(12) United States Patent
Engler et al.

(10) Patent No.: US 8,120,000 B2
(45) Date of Patent: Feb. 21, 2012

(54) MEASURING APPARATUS HAVING A MOVABLE MEASURING DEVICE IN A PRESS

(75) Inventors: Hans Engler, Dossenheim (DE); Michael Krüger, Edingen-Neckarhausen (DE); Manfred Schneider, Bad Rappenau (DE); Frank Schumann, Heidelberg (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 278 days.

(21) Appl. No.: 12/423,273

(22) Filed: Apr. 14, 2009

(65) Prior Publication Data

US 2009/0256087 A1 Oct. 15, 2009

(30) Foreign Application Priority Data

Apr. 14, 2008 (DE) .......................... 10 2008 018 913

(51) Int. Cl.
*G01N 21/86* (2006.01)
*H04N 1/04* (2006.01)

(52) U.S. Cl. ..................... 250/559.01; 358/488; 358/496

(58) Field of Classification Search .................. 250/205, 250/559.1, 559.14, 559.2, 208.1; 358/1.2, 358/1.9, 450, 474, 486–498; 399/49, 54, 399/180; 101/419, 230, 231, 232
See application file for complete search history.

(56) References Cited

U.S. PATENT DOCUMENTS

| | | | |
|---|---|---|---|
| 5,231,927 A | 8/1993 | Pfisterer et al. | |
| 5,471,309 A | 11/1995 | Bolza-Schünemann | |
| 5,607,121 A | 3/1997 | Boriani et al. | |
| 5,726,773 A * | 3/1998 | Mehlo et al. | 358/474 |
| 5,927,203 A * | 7/1999 | Gieser et al. | 101/419 |
| 6,222,949 B1 * | 4/2001 | Nakata | 382/298 |
| 7,034,928 B2 | 4/2006 | Tsukamoto et al. | |
| 7,398,733 B2 | 7/2008 | De Vries et al. | |
| 7,478,806 B2 | 1/2009 | Buck et al. | |
| 7,715,071 B2 * | 5/2010 | Takeda et al. | 358/518 |
| 2003/0095301 A1 * | 5/2003 | Berchtold et al. | 358/530 |
| 2005/0200919 A1 * | 9/2005 | Fukuda | 358/496 |
| 2007/0228307 A1 | 10/2007 | Muller | |
| 2008/0030717 A1 | 2/2008 | Engler et al. | |

FOREIGN PATENT DOCUMENTS

| | | |
|---|---|---|
| CN | 1499192 A | 5/2004 |
| CN | 1950210 A | 4/2007 |
| CN | 101118222 A | 2/2008 |
| DE | 2636 A | 11/1951 |
| DE | 1014125 A | 8/1957 |
| DE | 41 13 478 A1 | 10/1992 |
| DE | 42 17 942 A1 | 12/1993 |
| DE | 195 43 246 A1 | 5/1996 |
| DE | 10 2004 021 601 A1 | 12/2005 |
| DE | 10 2006 003 339 A1 | 8/2006 |
| DE | 10 2007 009 971 A1 | 10/2007 |
| DE | 10 2006 061 997 A1 | 6/2008 |

* cited by examiner

*Primary Examiner* — Georgia Y Epps
*Assistant Examiner* — Don Williams
(74) *Attorney, Agent, or Firm* — Laurence A. Greenberg; Werner H. Stemer; Ralph E. Locher

(57) ABSTRACT

A measuring apparatus for scanning moving, preferably sheet-like, printing materials in a printing material-processing machine, such as a press for processing sheet material. The apparatus has a measuring device which can be moved, at least in the transport direction of the printing materials. The measuring apparatus is set up in such a way that, during a measuring operation, the measuring device is moved over the moving printing material in the transport direction of the printing material with a differential speed relative to the transport speed of the printing material.

20 Claims, 5 Drawing Sheets

MEASURING APPARATUS HAVING A MOVABLE MEASURING DEVICE IN A PRESS

CROSS-REFERENCE TO RELATED APPLICATION

This application claims the priority, under 35 U.S.C. §119, of German application DE 10 2008 018 913.8, filed Apr. 14, 2008; the prior application is herewith incorporated by reference in its entirety.

BACKGROUND OF THE INVENTION

Field of the Invention

The invention lies in the printing and printing material-processing field. More specifically, the invention relates to a measuring apparatus for scanning moving, preferably sheet-like, printing materials in machines for processing printing materials. The apparatus has a measuring device which can be moved, at least in the transport direction of the printing materials.

Measuring apparatuses of this type are used to check the quality of printing materials during their production in a machine processing printing materials. In printing presses, measuring devices are normally installed in the last printing unit. The measuring devices register a printed sheet or a paper web still in the machine and perform measurements with regard to register accuracy, coincidence accuracy or inking. Since the printing material in the machine is led past the measuring device at high speed, the latter is not able to register all of the printing material because of the technical conditions in the current measuring sensors, but normally registers only print control strips applied in the edge region of the printing material. The measured color values registered on the print control strips are then compared with measured color values from the printing original, in the event of deviations between printing original and color measured values on the printing material, appropriate control interventions being made in the inking of the press. However, the reduction to the registration of lateral print control strips, as compared with the registration of the entire area of the whole of the printed image on the printing material, represents non-optimal registration. The control could be improved, in particular in the inking area, if the entirety of the area of the printing material could be registered by the measuring device. This is not possible, however, with the stationary measuring devices that are present in state of the art presses.

Such a stationary measuring device in presses is described, for example, in German published patent application DE 10 2004 021 601 A1 and its counterpart U.S. Pat. No. 7,398,733 B2. There, a press is shown which has a turning device, a stationary measuring device being accommodated in each case before the turning device in the last printing unit and after the turning device in the last printing unit. By using this measuring device, it is possible to register control elements in a color measuring strip both on the front side and on the reverse of a recto and verso printed sheet. However, registration of the entire area of the printed sheet on the printing material is not possible with the current measuring sensors, since the printing material is moved past the measuring device at too high a speed.

German published patent application DE 41 13 478 A1 and its counterpart U.S. Pat. No. 5,231,927 disclose an electronic sheet control apparatus for sheet-carrying cylinders in presses, which is fitted to a rotating cylinder transporting sheets. The sheet control apparatus comprises two linear CCD arrays, which register the positions of the sheet leading edge and in this way can register the position of the sheet with respect to the grippers on the cylinder. Using such a small CCD line array, however, only the position of the sheet edge can be registered but no registration of the printed image of the sheet transported on the cylinder is possible.

SUMMARY OF THE INVENTION

It is accordingly an object of the invention to provide a measurement device in a printing press which overcomes the above-mentioned disadvantages of the heretofore-known devices and methods of this general type and which provides a measuring apparatus for scanning moving printing materials in presses that permits scanning of the whole of the printed image on the printing material at full production speed in a press.

With the foregoing and other objects in view there is provided, in accordance with the invention, a measuring apparatus for scanning moving printing materials in a printing material-processing machine in which printing materials are transported in a transport direction, the apparatus comprising:

a measuring device movably mounted for movement in the transport direction of the printing materials; and wherein said measuring device, during a measuring operation, is moved over the moving printing material in the transport direction of the printing material at a differential speed relative to a transport speed of the printing material.

In other words, the objects of the invention are achieved with a measuring apparatus that has a movable measuring device which is moved over the moving printing material in the transport direction of the printing material. In this way, it is possible for the measuring device to follow the transport path of the moving printing material at least over a subsection, so that the residence time of the measuring device over the printing material can be prolonged in comparison with a stationary measuring device. This prolongation of the measuring operation of a printing material to be measured permits more comprehensive scanning of the printing material as far as scanning the entire area, i.e., the entire surface, of the printing material. The smaller the differential speed between the measuring device and the transport speed of the printing material, the longer is the measuring operation on the individual printing material. Given a sufficiently long residence time of the measuring device over the printing material, in this way registration of the entire area of the printing material is possible. This is possible in particular during the use of a spectral scanner as a measuring device which has at least a geometric resolution of 100 dpi, resolutions above 200 dpi being preferred. In this case, the spectral scanner preferably extends transversely with respect to the printing material transport direction over the entire width of the printing material, so that there is only relative movement between measuring apparatus and printing material in the direction of the transport direction of the printing material but no relative movement of the measuring device transversely with respect to the printing material transport direction. The measuring apparatus according to the invention is suitable both for the registration of sheet printing materials and for the registration of printed images on paper webs in web-fed presses or other machines from the graphics industry, such as punches, folding machines etc.

In an advantageous refinement of the invention, provision is made for the distance between the printing material and the measuring device to be largely constant during the measuring operation. It is possible to consider the measuring distance substantially constant if the fluctuations between printing material and measuring device do not amount to more than plus/minus 0.2 mm. Larger deviations lead to optical distortion and therefore to the impairment of the measurement results.

In accordance with a particularly advantageous feature of the invention, the measuring apparatus has guide elements parallel to the transport direction of the printing material. The substantially constant distance between the printing material and the measuring device is made possible by the guide elements that are arranged parallel to the transport direction of the printing material. The measuring device is mounted such that it can move in the guide elements and thus can be moved parallel to the transport direction of the printing material without vertical deviations effecting a change in the distance. In order to permit the necessary accuracy and uniform movement during registration of the printing material, the measuring device is preferably driven by a linear motor. To this end, the measuring apparatus has stator elements arranged parallel to the guide elements which, together with a runner which carries the measuring device, constitute a linear drive.

Furthermore, provision is made for there to be a printing material transport device which transports the printing material largely parallel to the direction of movement of the measuring device. Since the printing materials do not stand still in the press but are transported at high speed, it is important that the printing materials are transported largely parallel to the direction of movement of the measuring device during the measuring operation of the measuring apparatus. This is readily possible in particular when both the measuring device and printing material move in parallel, planar planes, so that neither printing material nor measuring device has to execute curved movements. Such a printing material transport device can be a sheet transport section in the delivery of a press. This sheet transport section has circulating gripper chains which carry gripper carriages having grippers. The grippers hold the printed sheets and guide these on the gripper chains parallel to the measuring device.

Additionally or alternatively, provision can be made that, during the measuring operation, the printing material is guided largely parallel to the direction of movement of the measuring device by means of blast air nozzles. In addition to the printing material transport device by means of gripper chains, already outlined, in particular printed sheets can also be guided past the measuring device via blast air nozzles. However, the blast air nozzles can also be employed in addition to the printing material transport device by means of gripper chains, in order to be better able to keep the distance between printing material and measuring device constant. In this case, the blast air nozzles assist the printing material transport device by means of gripper chains.

A further possible way of supporting the sheet consists in the printing material being guided on a supporting element, in particular on a tray, during the measuring operation. This refinement of the invention can be implemented alternatively or additionally to the printing material transport device with gripper chains and the transport and the support by means of blast air nozzles. In this refinement, the printing material is supported from below by a tray at least on a subsection during the measuring operation, in order in this way to keep the distance between printing material and measuring device constant.

In a particularly advantageous refinement of the invention, provision is made for the measuring apparatus to have at least two movable measuring devices. If there are two measuring devices on the same side of the printing material transport path, the measuring devices can divide up the scanning operation. This means that each measuring device, for example, has to measure only one half of a printing material. In this way, the measuring operation on the printing material can be prolonged further, so that the measurement accuracy increases. However, it is also possible for the at least one first measuring device and at least one second measuring device to register the printing materials alternately. In this case, each printing material is registered by only one measuring device, so that, for example, the first measuring device registers only the odd-numbered printed sheets while the second measuring apparatus registers the even-numbered sheets. Since there is in each case a short pause between two measuring operations during the registration of printing materials, it is more easily possible here to position the respective measuring device of the measuring apparatus back to its starting point again and to make it ready for the next measuring operation.

Advantageously, provision is additionally made for there to be at least one measuring device which registers the reverse of the printing material. If there are at least two measuring devices, one measuring device can scan the front side of the printing material while the other measuring device scans the reverse. In this way, printing materials produced by verso printing can also be registered on both sides in the machine. It is also possible for the measuring devices for front side and reverse to be located opposite each other, so that front side and reverse of the printing material are registered simultaneously. In this procedure, it is not the front side or the reverse that is registered first; instead the front side and the reverse can be registered simultaneously. In addition, this space-saving arrangement makes it possible to arrange a plurality of measuring devices in each case for the front side and reverse, so that the front side and reverse of the printing material can in each case be registered alternately by a measuring device, so that the measuring device which is currently not being used in each case can be moved into the starting position to carry out the next measuring operation.

Advantageously, provision is additionally made for the measuring apparatus to be connected to a computer for evaluating the data registered on the printing material by means of the measuring apparatus, and for the computer to act on the control system of the machine processing printing materials. The data registered by means of the measuring apparatus can thus be used immediately for driving a press. If the measuring apparatus carries out color measurements on the printing material, the measured color values registered by means of the measuring apparatus can be compared in the computer with the measured values from a printing original. If deviations lying outside the tolerance limit between printing original and printing material are determined, the computer can for example calculate appropriate actuating variables for adjusting settings in the inking unit of the press. These actuating variables are then sent to the actuating motors in the inking units of the press and effect a changed setting of the inking in the press.

In a particularly advantageous refinement of the invention, provision is made for the machine processing printing material to comprise a processing unit having a delivery for holding printing materials and for at least one measuring apparatus to be arranged between at least one processing unit and the delivery, in a transport path between processing unit and delivery. The processing unit can be a printing unit of a press or folding, punching or cutting units in machines for further print processing, which pass on printing materials following processing onto the transport path in a delivery which, in turn, stacks the printing materials produced on a delivery stack. This arrangement offers the advantage that the transport path between the processing unit and the delivery is relatively long and, in addition, rectilinear movement of the printing material is made possible. This rectilinear movement makes it easier to maintain a constant distance between printing material and measuring device. Should the distance between measuring device and printing material change despite this, then additional compensating means can be provided to set the distance between measuring device and printing material. For example, there can be a drive motor which controls the metering rate of the blast air nozzles and in this way regulates the distance between printing material and measuring device. In addition, the movable tray can change the distance between printing material and measuring device by means of a drive motor. Alternatively or additionally, the runner having the measuring device can also have compensating means which permit a vertical movement of the measuring device in relation to the sheet transport direction, so that the measuring device can be moved away from the printing material or toward the printing material. To this end, a small drive motor, which regulates the distance between printing material and measuring device, is provided on the runner.

In accordance with a concomitant feature of the invention, the machine for processing printing materials is a press with a plurality of printing units and a turning device between the printing units. In accordance with the invention, a measuring apparatus is disposed before the turning device and a further measuring apparatus is disposed after the last printing unit. Given this type of arrangement of the measuring apparatus in a press, the measuring apparatuses can in each case be used to register printed sheets in recto printing and in verso printing. In the case of verso printing, the measuring apparatuses are wired in such a way that the first measuring apparatus before the turning device registers the front side of the printing material, while the second measuring apparatus after the turning device after the last printing unit registers the reverse of the printing material. However, if the press is operated in pure recto printing, then both measuring apparatuses register the front side of the printing material, so that the measuring apparatuses can alternate during the scanning of a printing material, so that each measuring apparatus has to scan only each second printing material. Therefore, the registration accuracy of the measuring apparatuses can be increased, since moving the respective measuring device back for the next measuring operation in the measuring apparatuses can always take place in the phase during which the respective measuring apparatus is currently not scanning any printing material.

Other features which are considered as characteristic for the invention are set forth in the appended claims.

Although the invention is illustrated and described herein as embodied in a measuring apparatus for a printing-material processing machine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
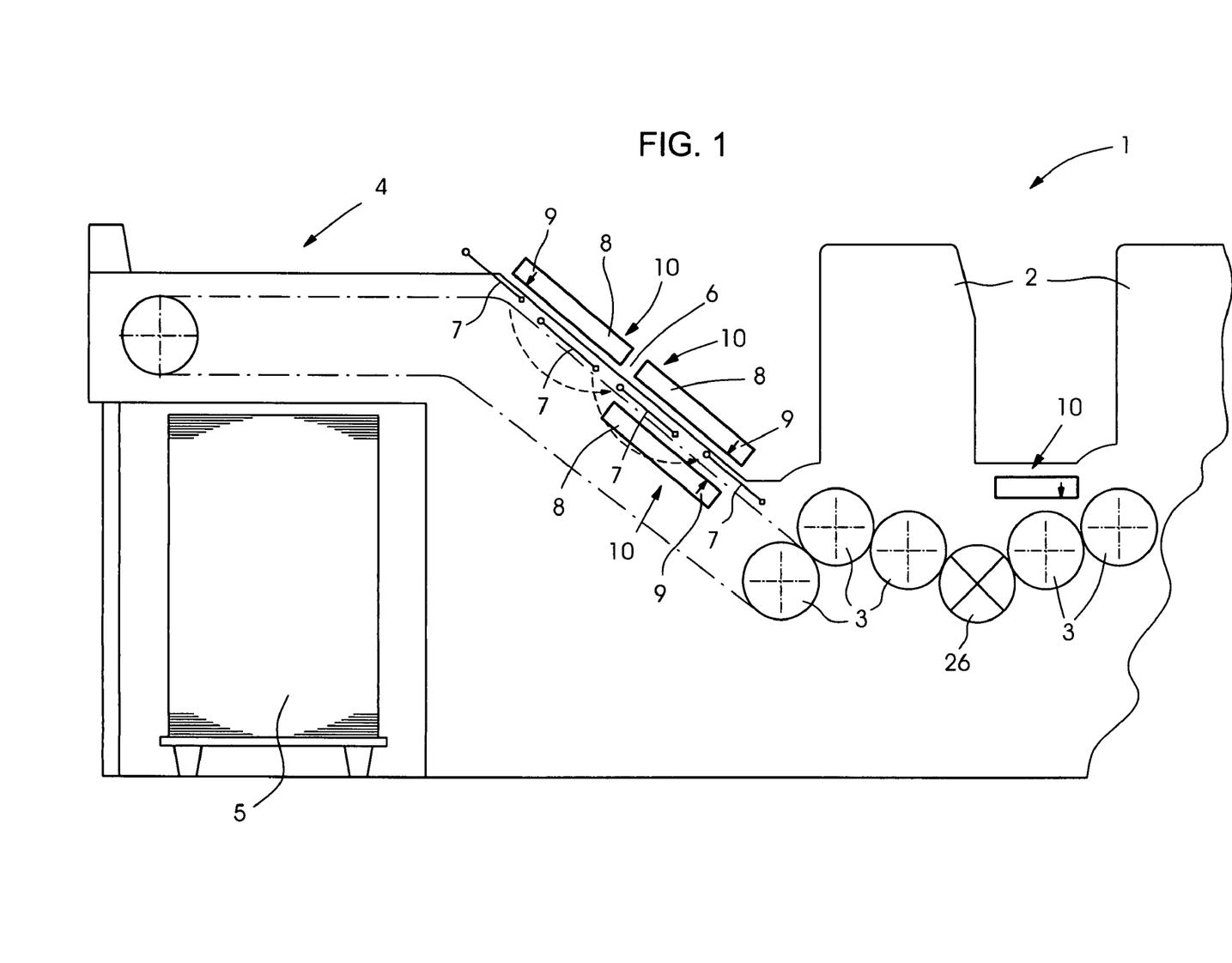
FIG. 1 shows a schematically drawn press and the delivery area adjacent thereto with two measuring devices.

Referring now to the figures of the drawing in detail and first, particularly, to FIG. 1 thereof, there is shown, in schematic format, a press 1 with two printing units 2 and a delivery 4. In the press 1, printed sheets 7 are transported through the machine by way of transport cylinders 3 and a turning device 26. The turning device 26 between the printing units 2 makes it possible to turn the printed sheet 7 between the printing units 2 and in this way to change between recto and verso printing. At the output from the last printing unit 2, the sheets 7 are transferred to a sheet transport section 6. This sheet transport section 6 connects the last printing unit 2 to the delivery 4, where the printed sheets 7 are deposited on the delivery stack 5. In this case, the sheet transport section 6 runs over a great distance in a planar plane, so that the printed sheets 7 carry out a rectilinear movement. Two measuring devices 10 are disposed above the sheet transport section 6. The measuring devices 10 have linear drives. The linear drive in each case comprises a stator 8 and a runner 9. The stator 8 is arranged fixedly above the sheet transport section 6, while the runner 9 is movable and carries the measuring optics 15. By means of the linear drive 8, 9, it is possible for the measuring optics 15 to be moved concomitantly in parallel in the sheet transport direction during the measuring operation, so that the time of the measuring operation can be prolonged. Following registration of a printed sheet 7, the runner 9 of the linear drive is moved back into its initial position, in each case counter to the transport direction of the printing materials 7, in order to be able to begin a renewed measuring operation on the next printed sheet 7. Furthermore, a third measuring device 10, which is constructed in the same manner, is arranged underneath the sheet transport section 6. The third measuring device 10 is configured to register the reverse of the printed sheets 7. In this way, it is possible to register the front side and reverse of a printed sheet 7 produced in verso printing. Of course, even more than the measuring devices 10 depicted in FIG. 1 can also be arranged along the sheet transport section 6. By means of the two measuring devices 10 arranged above the sheet transport section 6, it is possible for not every printed sheet 7 to have to be scanned by each measuring device 10 but for each measuring device 10 to scan only each second printed sheet 7, so that, accordingly, more time remains for moving the runner 9 into its initial position after the measuring operation.

The runners 9 of the measuring device 10 in this case move at a certain relative speed, the speed $v_M$, in relation to the transport speed $v_u$ of the sheets 7. Given a measuring section with a length s=1.4 m and a sheet length l=0.7 m with a gripper/sheet transport speed $v_u$=5 m per second and a differential speed of $v_M$=1.66 m per second, the result, by way of example, is thus a measuring time t=0.42 seconds.

Figure 2:
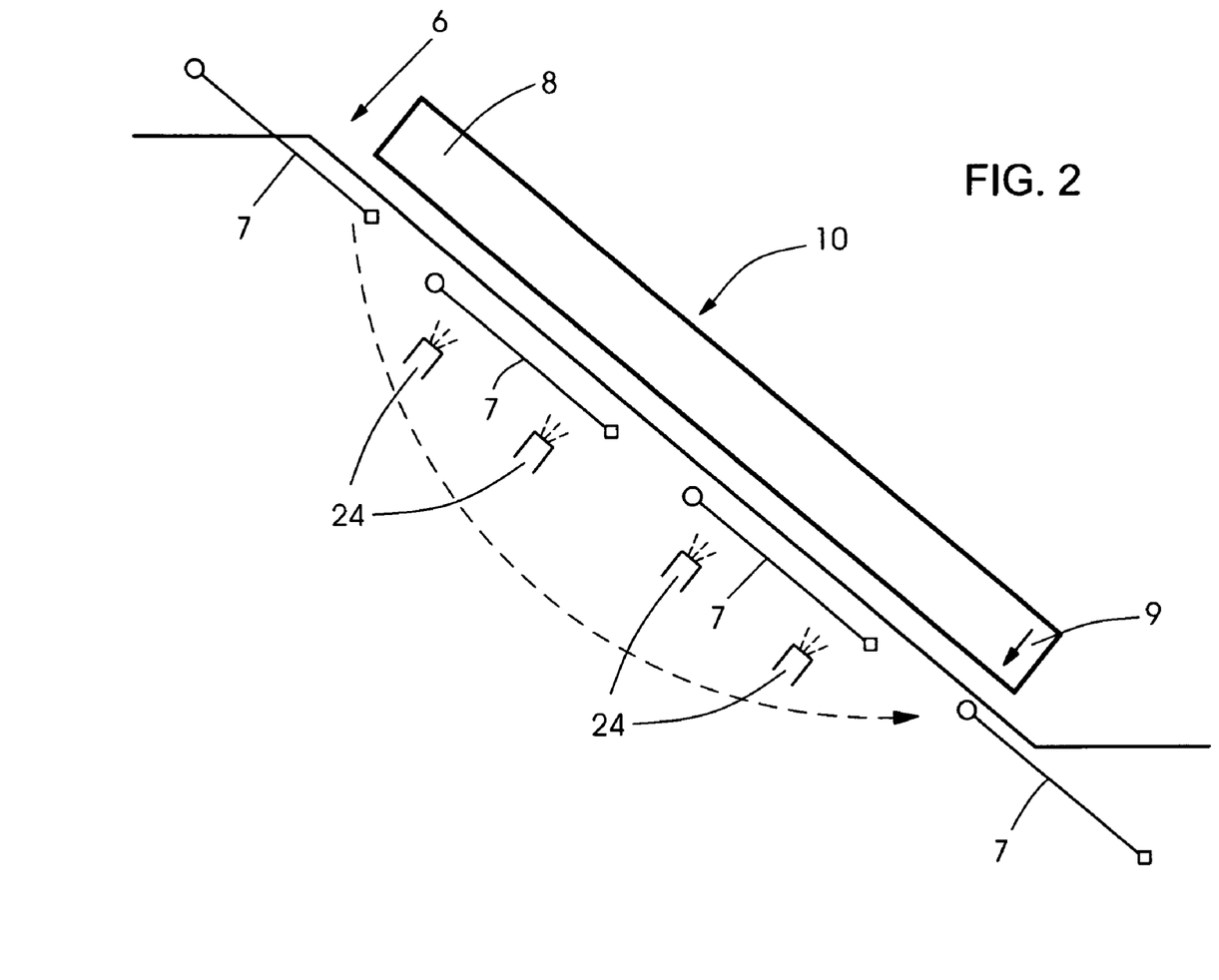
FIG. 2 shows the transport path in the delivery area with a measuring device.

In FIG. 2, there is only one measuring device 10 above the sheet transport section 6, this being designed to be appropriately longer as compared with the two measuring devices 10 in FIG. 1. For this purpose, the measuring device 10 in FIG. 2 must scan each printed sheet 7. Given the same sheet length l, the same sheet transport speed $v_0$ and a measuring section s=2.8 m, with a differential speed $v_M$=1 m per second, the result is a measuring time t=0.7 seconds. This is significantly longer than the measuring time in FIG. 1. Furthermore, blast air nozzles 24 are shown in FIG. 2, which ensure that the distance between printed sheets 7 and measuring device 10 remains constant. The blast air nozzles can be controlled or closed-loop controlled in order to be able to set the distance between printed sheets 7 and measuring device 10.

Figure 3:
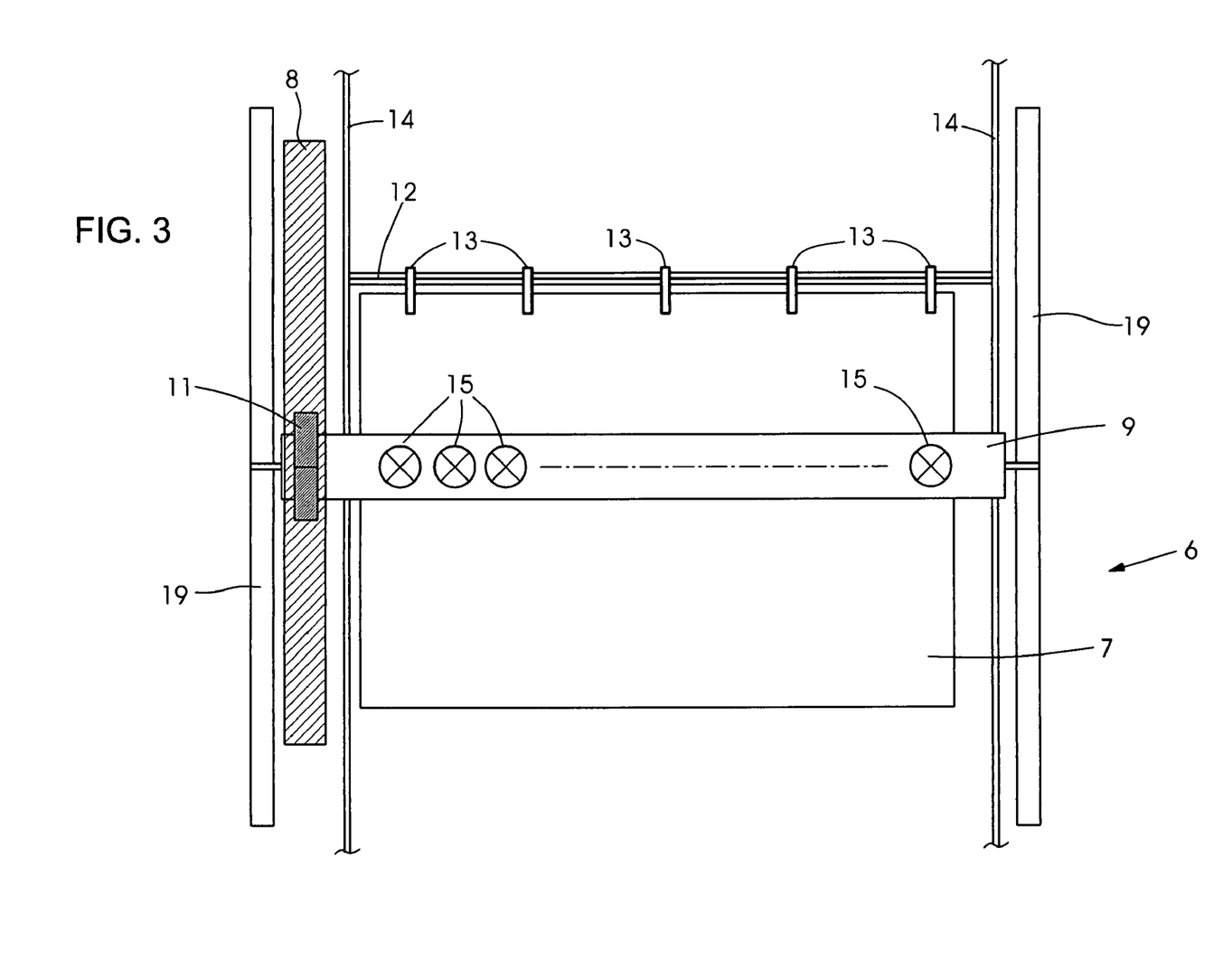
FIG. 3 shows gripper chains in the delivery in plan view from above.

FIG. 3 shows the plan view of a measuring apparatus according to the invention, which is arranged between the last printing unit 2 and the delivery 4. In the plan view of the sheet transport section 6, it can be seen that, during the measuring operation, printing materials 7 are guided by a gripper carriage 12, which in turn is guided laterally on gripper chains 14. On the gripper carriage 12 there are grippers 13, which hold the printed sheet 7 firmly. Parallel to the gripper chains 14 there run linear drive guides 19, in which the runner of the linear drive 9 is guided in parallel in the sheet transport direction. In the lateral area, the runner 9 has a magnet 11 which, together with the stator 8 of the linear drive, effects the drive of the runner 9. In this way, the runner 9 having the measuring beam 15 can be moved between the gripper chains 14, parallel to the direction of movement of the printed material 7 and thus register the printing material 7 at the corresponding differential speed $v_M$.

Figure 4:
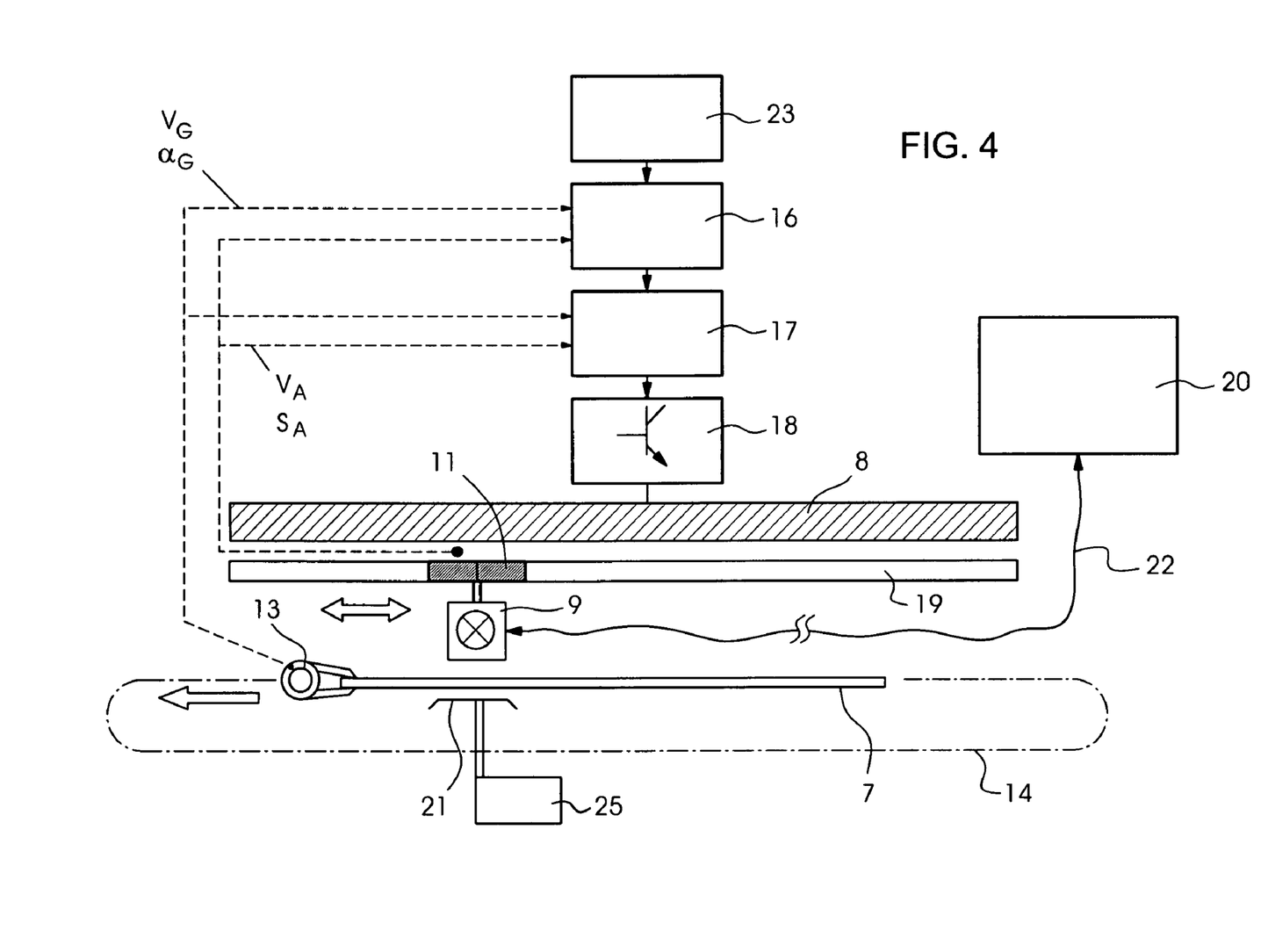
FIG. 4 shows a measuring device according to the invention in side view and also the necessary controlled systems.

In FIG. 4, the side view is illustrated, slightly modified in relation to the embodiment in FIG. 3. In the lower half, once more the lateral linear guide 19 can be seen, in which the runner 9 of the linear motor with the measuring beam 15 is guided. The measuring beam 15 in this case extends over the entire width of the printed sheet 7 and is designed as a spectral scanning device with at least 200 dpi geometric resolution. The measuring beam 15 can be moved to and fro by the linear drive in relation to the transport direction of the printed sheet 7. During the measuring operation, the printed sheet 7 can additionally be supported by a tray-like measuring support 21, in order to keep the distance between measuring device 10 and printed sheet 7 constant. The measuring support 21 is moved concomitantly with the sheet 7 and is additionally designed to be vertically adjustable by means of an adjusting element 25, so that the distance between printed sheet 7 and measuring device 10 can be regulated. In addition, the measuring beam 15 is connected in a wire-free or wire-bound manner via a communication link 22 to a computer 20, which acquires the measured data from the measuring beam 15 and processes it in order to drive actuating drives in the press 1. For example, the computer 20 can compare the acquired measured values with the measured values from a printing original and, in the event of deviations outside the tolerance, can undertake corresponding control interventions, for example in the inking units of the printing units 2 in the press 1.

In the upper half of FIG. 4, the controlled sections for driving the linear drive comprising stator 8 and runner 9 are additionally shown. Used as input variables for the controlled section are the setpoints for the pre-definition of the differential speed, also called the measuring speed, $v_M$, and the return travel speed $v_2$ at which the measuring beam 15 is moved back into the initial position after a measuring operation. These entered setpoints 23 are supplied to a measuring section controller 16 and a speed controller 17, to which in turn the actual values of the transport speed of the printed sheet 7 $v_G$, of the angle of the grippers $\alpha_G$ and also the speed of the linear drive $v_A$ and the section position of the linear drive $s_A$ are also fed. From the setpoints and actual values, the controllers 16, 17 calculate the appropriate actuating variables for the power electronics 18 for driving the linear drive 8, 9. The power electronics 18 in turn convert the actuating variables to corresponding currents for driving the linear drive 8, 9.

Figure 5:
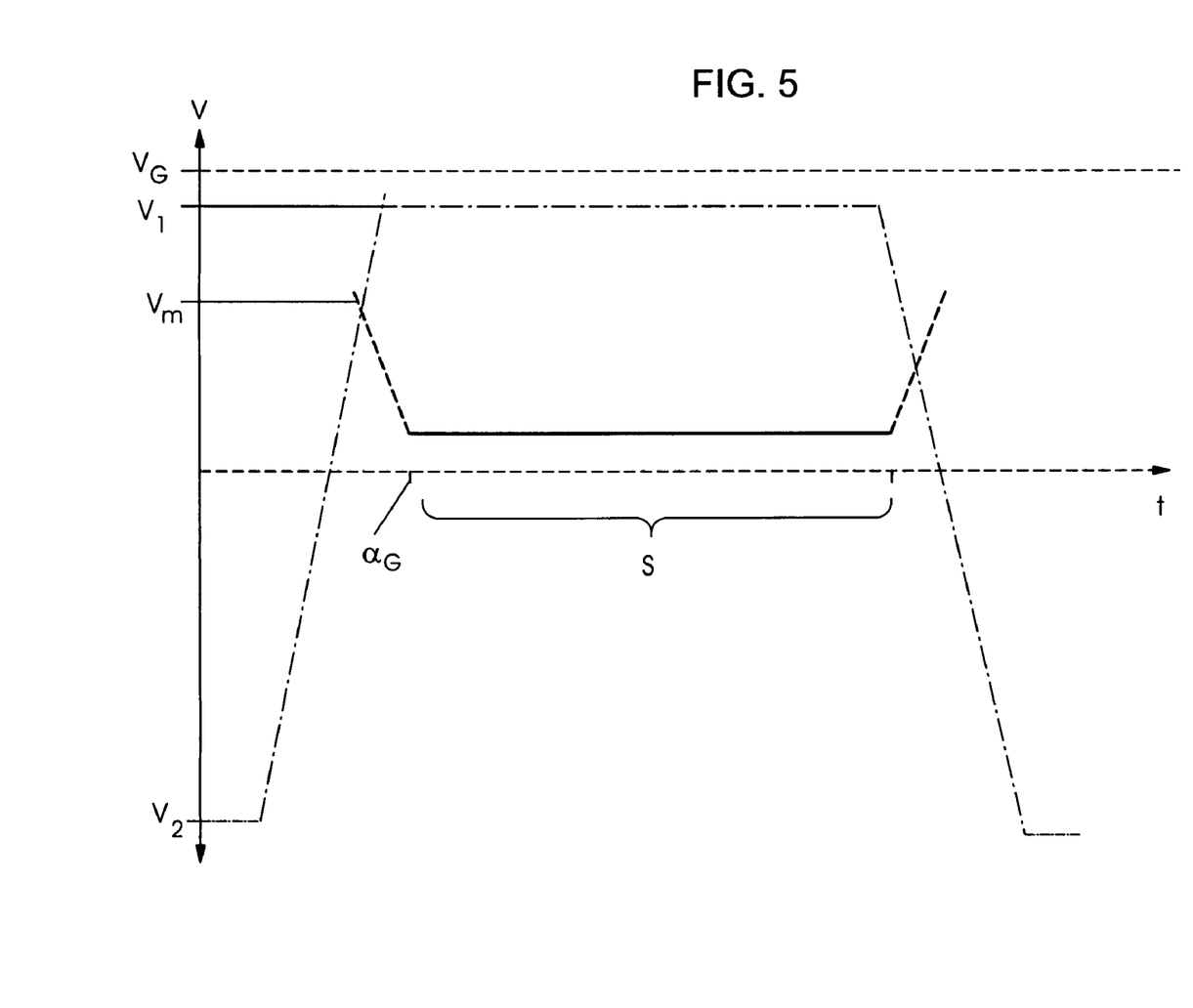
FIG. 5 shows an overview of the speed variations during a measuring operation.

In FIG. 5, the speed variation v over the time t for a measuring operation is depicted by way of example. It can be seen that the speed of the printed sheet 7 $v_G$, which coincides with the speed of the grippers and therefore the sheet transport speed, is constant. During the measuring operation, the measuring beam 15 likewise moves at a constant travel speed $v_1$, which results in the measuring speed $v_M$ drawn thickly in black. Following the conclusion of a measuring operation, the measuring beam 15 is moved back into its initial position at a return speed $v_2$ and the next measuring operation can begin. Depending on the set speeds $v_G$, $v_1$ and the measuring travel s, the result is the corresponding measuring time t.

The invention claimed is:

1. A measuring apparatus for scanning moving printing materials in a printing material-processing machine in which printing materials are transported in a transport direction, the apparatus comprising:
   a measuring device movably mounted for movement in the transport direction of the printing materials; and
   wherein said measuring device, during a measuring operation, is moved over the moving printing material in the transport direction of the printing material at a differential speed relative to a transport speed of the printing material.

2. The measuring apparatus according to claim 1, wherein said measuring device is configured to register an entire area of the printing material.

3. The measuring apparatus according to claim 1, wherein said measuring device includes a spectral scanner with a geometric resolution of at least 200 dpi.

4. The measuring apparatus according to claim 1, wherein a distance between the printing material and said measuring device is substantially constant during the measuring operation.

5. The measuring apparatus according to claim 1, which comprises guide elements extending parallel to the transport direction of the printing material.

6. The measuring apparatus according to claim 5, which comprises a linear motor configured to move said measuring device in said guide elements.

7. The measuring apparatus according to claim 1, wherein the printing material is transported by way of a printing material transport device substantially parallel to the direction of movement of said measuring device.

8. The measuring apparatus according to claim 7, wherein said printing material transport device comprises gripper chains, grippers, and gripper carriages.

9. The measuring apparatus according to claim 7, which comprises blast air nozzles disposed to guide the printing material, during the measuring operation, substantially parallel to the direction of movement of said measuring device.

10. The measuring apparatus according to claim 7, which comprises a supporting element for guiding the printing material during the measuring operation.

11. The measuring apparatus according to claim 10, wherein said supporting element is a tray.

12. The measuring apparatus according to claim 1, wherein said measuring device is one of at least two movable measuring devices.

13. The measuring apparatus according to claim 12, wherein said measuring devices include at least one first measuring device and at least one second measuring device registering the printing materials alternately.

14. The measuring apparatus according to claim 1, which further comprises at least one measuring device disposed to register a reverse side of the printing material.

15. The measuring apparatus according to claim 14, wherein at least two measuring devices are disposed to simultaneously register a front side and a reverse side of the printing material.

16. The measuring apparatus according to claim 1, which comprises a computer connected to said measuring device for evaluating data obtained by registering the printing material, said computer acting on a control system of the printing material-processing machine.

17. A printing material-processing machine, comprising at least one measuring apparatus according to claim 1.

18. The machine according to claim 17, comprising at least one processing unit and a delivery for holding printing materials, wherein said at least one measuring apparatus is disposed between said processing unit and said delivery, in a transport path formed between said processing unit and said delivery.

19. The machine according to claim 18, wherein said measuring apparatus includes compensating means for setting a spacing distance between said measuring device and the printing material.

20. A printing press, comprising:
   a plurality of printing units and a turning device disposed between said printing units; and
   a measuring apparatus according to claim 1 disposed before said turning device in a transport direction through the printing press and a further measuring apparatus following a last printing unit of said plurality of printing units.

* * * * *